United States Patent [19]
Neumann et al.

[11] Patent Number: 6,121,485
[45] Date of Patent: Sep. 19, 2000

[54] METHOD OF PREPARING N-PHOSPHONOMETHYL GLYCINE

[75] Inventors: Thomas Neumann, Trostberg; Frank Fleischer, Palling; Jürgen Graefe, Trostberg; Benedikt Hammer, Tacherting, all of Germany

[73] Assignee: SKW Trostberg Aktiengesellschaft, Trostberg, Germany

[21] Appl. No.: 09/194,953

[22] PCT Filed: Jul. 22, 1997

[86] PCT No.: PCT/EP97/03955

§ 371 Date: Dec. 7, 1998

§ 102(e) Date: Dec. 7, 1998

[87] PCT Pub. No.: WO98/03517

PCT Pub. Date: Jan. 29, 1998

[30] Foreign Application Priority Data

Jul. 24, 1996 [DE] Germany .............. 196 29 870

[51] Int. Cl.[7] ..................................... C07F 9/38
[52] U.S. Cl. ............................................. 562/17
[58] Field of Search ........................ 562/17, 11

[56] References Cited

U.S. PATENT DOCUMENTS

| 4,221,583 | 9/1980 | Gaertner et al. |
| 4,439,373 | 3/1984 | Nagubandi. |
| 4,548,760 | 10/1985 | Nagubandi. |
| 4,657,705 | 4/1987 | Miller. |
| 5,679,843 | 10/1997 | Hodgkinson ............... 562/17 |
| 5,750,774 | 5/1998 | Miyata ....................... 562/17 |
| 5,948,937 | 9/1999 | Worley ....................... 562/17 |

FOREIGN PATENT DOCUMENTS

| 0112580 | 7/1984 | European Pat. Off. |
| 9615135 | 5/1996 | WIPO. |

*Primary Examiner*—Gary Geist
*Assistant Examiner*—Jean F Vollano
*Attorney, Agent, or Firm*—Fulbright & Jaworski, LLP

[57] ABSTRACT

To prepare N-phosphonomethyl glycine, a) aminomethylphosphonic acid or one of its salts in water, if necessary or desirable with the addition of lyes, is reacted with an alkali carbonate and/or alkali hydrogencarbonate or with carbon dioxide and a lye, b) the resulting alkali salt of N-phosphonomethylcarbamic acid is subsequently hydroxymethylated with formaldehyde, c) the salts, resulting from b), of N-hydroxymethyl-N-phosphonomethyl-carbamic acid, if necessary or desirable with addition of a lye, are reacted with hydrocyanic acid and/or a cyanide and d) the N-carboxy-N-phosphonomethylglyconitrile salts thus obtained are treated with acids and converted by means of hydrolysis and decarboxylation into N-phosphonomethyl glycine.

In this way, it is possible to obtain excellent yields of high-purity N-phosphonomethyl glycine.

17 Claims, No Drawings

METHOD OF PREPARING N-PHOSPHONOMETHYL GLYCINE

This application is the national phase of PCT/EP97/03955 filed Feb. 22, 1997.

The subject matter of the invention is a method of preparing N-phosphonomethyl glycine from aminomethylphosphonic acid or one of its salts.

N-phosphonomethyl glycine (glyphosate) has been in use for more than 20 years as a systemic herbicide, the action of which is based on inhibition of the plant enzyme 5-enolpyruvylshikimat-3-phosphate synthetase (EPSP synthetase) and thus of aromatic amino acid synthesis.

Of the many syntheses which have been developed for N-phosphonomethyl glycine, technical significance has been attached, amongst other reactions, to reactions in which an amino component is hydroxymethylated or cyanomethylated by reacting it with formaldehyde or with formaldehyde and hydrocyanic acid respectively.

A familiar disadvantage of the hydroxymethylation and cyanomethylation of primary amines is that one usually obtains mixtures of mono- and di-substituted products.

According to the Polish patent PL 156 933, for example, in which aminomethylphosphonic acid is reacted with formalin and sodium cyanide at a pH of 10, and the initially formed nitriles are subsequently hydrolysed, one obtains not only the main product N-phosphonomethyl glycine, but also the by-product N-phosphonomethyliminodiacetic acid. U.S. Pat. No. 4,221,583 describes the reaction of aminomethylphosphonic acid with formaldehyde and sodium cyanide at pH levels of 6.6 to 9.7; in this case, the yield of N-phosphonomethylglyconitrile is only 65%.

During hydroxymethylation and analogous reactions of primary amines it should be possible to prevent the formation of di-substituted products by introducing a protective group temporarily into the amine. A synthesis of this kind, in which N-phosphonomethyl glycine is obtained from glycine, is disclosed in European patent 112 580. When glycine is reacted with sodium carbonate, it is first converted into the sodium salt of the corresponding carbamic acid. Subsequent reaction with formalin and diethyl phosphite leads to formation of N-carboxy-N-(O,O'-diethylphosphonomethyl)glyconitrile, from which N-phosphonomethyl glycine is obtained by way of hydrolysis. However, the 36% yield from this method is also extremely low.

The object of the invention is thus to provide a technically uncomplicated method of preparing N-phosphonomethyl glycine, which does not have the disadvantages of the prior art and with which high yields of high-purity compound are obtained.

This object is established according to the invention in that a) aminomethylphosphonic acid or one of its salts in water, if necessary or desirable with the addition of lyes, is reacted with an alkali carbonate and/or alkali hydrogencarbonate or with carbon dioxide and a lye, b) the resulting alkali salt of N-phosphonomethylcarbamic acid is hydroxymethylated with formaldehyde, c) the salts, resulting from b), of N-hydroxymethyl-N-phosphonomethylcarbamic acid, if necessary or desirable with addition of a lye, are reacted with hydrocyanic acid and/or a cyanide and d) the N-carboxy-N-phosphonomethylglyconitrile salts thus obtained are treated with acids and converted by means of hydrolysis and decarboxylation into N-phosphonomethyl glycine.

Surprisingly, one obtains an excellent yield of high-purity N-phosphonomethyl glycine in this way, with relatively uncomplicated technical equipment. What is especially surprising is that during the reaction only very small proportions (<0.5%) of N-phosphonoethyliminodiacetic acid are formed, and none is contained in the isolated N-phosphonomethyl glycine.

According to the invention, N-phosphonomethyl glycine is prepared from aminomethylphosphonic acid in a number of steps; however, as per a special embodiment, the intermediates need not be isolated and the entire process can be carried out as a one-pot reaction.

In the first step a), aminomethylphosphonic acid or one of its salts in water—if necessary or desirable with the addition of lyes—is reacted with an alkali carbonate and/or alkali hydrogencarbonate, or with carbon dioxide and a lye; the amino group is carboxylated, and salts of N-phosphonomethylcarbamic acid are formed, having the formula (I):

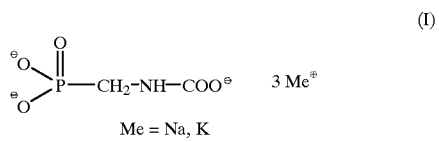

$$\text{Me} = \text{Na}, \text{K}$$

Since the reaction ensues in water, it is preferable to use a water-soluble alkali carbonate and/or alkali hydrogencarbonate. Particular preference is given to sodium and potassium salts, some of which can also be used in the form of their hydrates. As lye, use is made preferably of sodium or potassium hydroxide solution. Instead of making direct use of alkali carbonate and/or alkali hydrogencarbonate, it is also possible to react the aminomethylphosphonic acid in water with carbon dioxide and a lye.

It is an essential feature of the invention that reaction step a) be carried out in water. The pH can be varied within wide limits and assume values preferably between 7 and 14; it is more preferable still if the pH is between 9 and 11. Where use is made of alkali carbonates and/or alkali hydrogencarbonates, the pH can be adjusted to a higher value if so desired by addition of lye.

The molar ratio of aminomethylphosphonic acid or one of its salts to alkali carbonate or alkali hydrogencarbonate can also be varied within wide limits. A molar ratio of 0.9 to 1.2 is preferred. The easiest way to adjust the pH to the desired value is to add suitable quantities of a lye either before or during the reaction.

For reaction step a) the temperature is not critical. It is preferably between 0 and 80° C. Too high a temperature, however, should be avoided in order to prevent decarboxylation of the carbamic acid or its salts. An especially preferred embodiment provides for a reaction temperature of 10 to 30° C.

The concentration of the reaction mixture in step a) is also largely unproblematic. A concentration range from 10 to 30 wt. %, calculated in terms of the aminomethylphosphonic acid or the corresponding salt, is recommended.

In reaction step b), the N-phosphonomethylcarbamic acid salt formed during step a) is reacted, preferably without prior isolation, with formaldehyde to form a salt—with the formula (II)—of N-hydroxymethyl-N-phosphonomethylcarbamic acid.

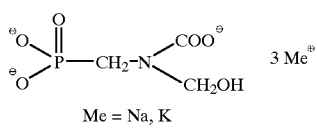

(II)

Me = Na, K

Insofar as is necessary, the pH is adjusted to a level in the range from 7 to 14, preferably 9 to 11, by simultaneous addition of lye. To this end, sodium or potassium hydroxide solution are used to good effect.

The formaldehyde can be used in the form of an aqueous solution (formalin) or in the form of paraformaldehyde. The molar ratio of formaldehyde to the aminomethylphosphonic acid used in step a) is preferably between 0.9 and 1.2.

For reaction step b), the temperature is again not critical, preferably being between 0 and 80° C. Too high a temperature, however, should be avoided in order to prevent decarboxylation of N-hydroxymethyl-N-phosphonomethylcarbamic acid or its salts. According to an especially preferred embodiment, therefore, the reaction temperature is adjusted to within the range from 10 to 30° C.

In reaction step c), the N-hydroxymethyl-N-phosphonomethylcarbamic acid salt formed during step b) is reacted—preferably without prior isolation—in aqueous alkaline solution with hydrocyanic acid or a cyanide to form a salt of N-carboxy-N-phosphonomethylglyconitrile with the formula (III).

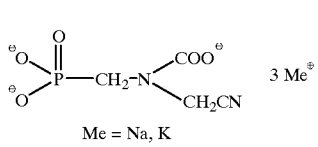

(III)

Me = Na, K

Where use is made of cyanides, the water-soluble alkali cyanides, such as sodium and potassium cyanide, are preferred. The molar ratio of hydrocyanic acid or cyanide to the aminomethylphosphonic acid used in step a) is preferably in the range from 0.9 to 1.5.

For carrying out step c), it is of advantage to select the reaction temperature and the pH such that they correspond to the conditions under which step b) is conducted. This avoids the possible need for time-consuming reaction-control modifications. If necessary or desirable, the pH can be kept constant by simultaneous metering of a lye—preferably sodium or potassium hydroxide solution.

In reaction step d) of the method of the invention, the N-carboxy-N-phosphono-methylglyconitrile salt formed in step c) is treated with acids. Following decarboxylation and hydrolysis of the nitrile group, the desired N-phosphonomethyl glycine (IV) is formed.

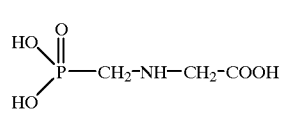

(IV)

The acids used are preferably common inorganic or organic acids, eg, hydrochloric, sulfuric, nitric and phosphoric acids, or formic and acetic acids. According to a preferred embodiment, use is made of concentrated aqueous hydrochloric acid in a molar ratio of about 4 to 8 to the aminomethylphosphonic acid used in step a).

Reaction step d) is preferably carried out at a temperature of 80 to 120° C. in order to ensure a high reaction rate.

N-phosphonomethyl glycine can be isolated using familiar methods from the reaction mixture obtained from step d). The following two techniques, however, are preferred:

First of all, the reaction mixture is freed of the aqueous hydrochloric acid by means of familiar methods; the residue is taken up in hot water and the pH adjusted with bases, especially sodium hydroxide solution, to 1.5 to 3.0. When the solution is cooled, the desired reaction product precipitates in the form of a fine crystalline powder. This may be washed, if necessary, with water and dried under vacuum.

Alternatively, following removal of excess salts, methanol can be added to the solution of N-phosphonomethyl glycine in hot water; as the mixture cools, the product crystallizes out as a fine powder.

With the method of the invention, which comprises several reaction steps but which, as already described, can be carried out as a one-pot reaction, and which is relatively easy to implement for industrial-scale production, one obtains yields of N-phosphonomethyl glycine of up to 88% of the theoretical yield (calculated in terms of aminomethylphosphonic acid) and a purity level of about 97 to 98%.

The following examples serve to explain the invention in more detail.

EXAMPLE 1

11.1 g (0.1 mol) aminomethylphosphonic acid are suspended in 35 g water and the pH is adjusted to 2.6 by addition of 25% sodium hydroxide solution. At a temperature of 20° C., 28.9 g (0.1 mol) sodium carbonate decahydrate are added. On completion of the addition, the pH of the solution is adjusted to 10 with 25% sodium hydroxide solution. Within a period of 38 minutes and at a temperature of about 20° C., 11.0 g of a 30% formalin solution are added to the reaction solution, together with 25% sodium hydroxide solution (pH 10). On completion of the addition, altogether 20 g (0.12 mol) of 25% sodium hydroxide solution have been consumed. Over a period of 11 minutes, 2.97 g (0.11 mol) hydrocyanic acid are added dropwise to the 20° C. solution, which is then left to stand for 2 h at room temperature. The pH remains at 10 during and after the addition of hydrocyanic acid.

To effect hydrolysis, the reaction mixture is blended carefully with 79 g (0.8 mol) of 37% aqueous hydrochloric acid. When no more gas is generated, the mixture is refluxed for 6 h before being boiled to dryness. The residue is digested in 68 g of 37% hydrochloric acid and the mixture then filtered. The filtrate is boiled down, and the resulting residue taken up in about 60 ml of boiling water. The clear solution is added to 60 ml methanol and the mixture cooled to about 5° C., whereupon the product crystallizes out as a fine powder. This is separated off by filtration, washed free of chloride with some 58 g water, and then dried at about 50° C. under vacuum.

One obtains 12.8 g N-phosphonomethyl glycine (77.5% of the theoretical yield calculated in terms of aminomethylphosphonic acid), with a tritrimetrically determined content of 97.7%. Ion chromatography shows the combined aqueous filtrates still to have a 10.5% content of N-phosphonomethyl glycine, which can be isolated in the usual way.

EXAMPLE 2

1.1 g (0.1 mol) aminomethylphosphonic acid are suspended in 35 g water and the pH is adjusted to 2.6 by addition of 25% sodium hydroxide solution. At a temperature of 20° C., 28.9 g (0.1 mol) sodium carbonate decahydrate are added. On completion of the addition, the pH of the solution is adjusted to 10 with 25% sodium hydroxide solution. Within a period of 40 minutes and at a temperature of about 21° C., 3.3 g (0.11 mol) paraformaldehyde are added to the reaction solution, together with 25% sodium hydroxide solution (pH 10). On completion of the addition, altogether 18.2 g (0.11 mol) of 25% sodium hydroxide solution have been consumed. Over a period of 11 minutes, 2.97 g (0.11 mol) hydrocyanic acid are added dropwise to the 21° C. solution, which is then left to stand for 1 h at room temperature. The pH remains at 10 during and after the addition of hydrocyanic acid.

To effect hydrolysis, the reaction mixture is blended carefully with 79 g (0.8 mol) of 37% aqueous hydrochloric acid. When no more gas is generated, the mixture is refluxed for 6 h before being boiled to dryness. The residue is digested in 68 g of 37% hydrochloric acid and the mixture then filtered. The filtrate is boiled down, and the resulting residue taken up in about 65 ml of boiling water. The clear solution is added to 65 ml methanol and the mixture cooled to about 5° C., whereupon the product crystallizes out as a fine powder. This is separated off by filtration, washed free of chloride with some 72 g water, and then dried at about 50° C. under vacuum.

One obtains 12.7 g N-phosphonomethyl glycine (77.7% of the theoretical yield calculated in terms of aminomethylphosphonic acid), with a tritrimetrically determined content of 97.3%. Ion chromatography shows the combined aqueous filtrates still to have an 8.7% content of N-phosphonomethyl glycine, which can be isolated in the usual way.

EXAMPLE 3

11.1 g (0.1 mol) aminomethylphosphonic acid are suspended in 35 g water. At a temperature of 20° C., 28.9 g (0.1 mol) sodium carbonate decahydrate are added.

On completion of the addition, the pH of the solution is adjusted to 10 with 25% sodium hydroxide solution. Within a period of 35 minutes and at a temperature of about 22° C., 3.3 g (0.11 mol) paraformaldehyde are added to the reaction solution, together with 25% sodium hydroxide solution. On completion of the addition, altogether 15.9 g (0.1 mol) of 25% sodium hydroxide solution have been consumed. Over a period of 10 minutes, 2.97 g (0.11 mol) hydrocyanic acid are added dropwise to the 22° C. solution, which is then left to stand for 2 h at room temperature. The pH remains at 10 during and after the addition of hydrocyanic acid.

To effect hydrolysis, the reaction mixture is blended carefully with 79 g (0.8 mol) of 37% aqueous hydrochloric acid. When no more gas is generated, the mixture is refluxed for 6 h before being boiled to dryness. The residue is taken up in about 70 g of boiling water, and the pH adjusted to 2 with 50% sodium hydroxide solution. When the mixture is cooled, the product crystallizes out as a fine powder. This is separated off by filtration, washed free of chloride with some 75 g water, and then dried at about 50° C. under vacuum.

One obtains 10.7 g N-phosphonomethyl glycine (63.9% of the theoretical yield calculated in terms of aminomethylphosphonic acid), with a tritrimetrically determined content of 95.8%. Ion chromatography shows the combined aqueous filtrates still to have a 24% content of N-phosphonomethyl glycine. The solution does not contain any N-phosphonomethyliminodiacetic acid.

What is claimed is:

1. A method of preparing N-phosphonomethyl glycine, comprising
    a) reacting aminomethylphosphonic acid or one of its salts in water, with an alkali carbonate, an alkali hydrogencarbonate, or with carbon dioxide and a lye,
    b) hydroxy-methylating the resulting alkali salt of N-phosphonomethyl carbamic acid with formaldehyde to form salts of N-hydroxymethyl-N-phosphonomethyl-carbamic acid;
    c) reacting said salts of N-hydroxymethyl-N-phosphonomethyl-carbamic acid, with hydrocyanic acid or a cyanide and
    d) treating the resultant N-carboxy-N-phosphonomethylglyconitrile salts with acids and converting by means of hydrolysis and decarboxylation into N-phosphonomethyl glycine.

2. The method of claim 1, wherein sodium or potassium hydroxide solution is used as lye.

3. The method of claim 1, wherein the alkali carbonate or alkali hydrogencarbonate is a water-soluble sodium or potassium compounds.

4. The method of claim 1, wherein step a) is carried out in aqueous solution at a pH of 7 to 14.

5. The method of claim 1, wherein use is made of 0.9 to 1.2 mol alkali carbonate or alkali hydrogencarbonate, or of $CO_2$, per mol of aminomethylphosphonic acid (salt).

6. The method of claim 1, wherein step a) is carried out at a temperature from 0 to 80° C.

7. The method of claim 1, wherein the concentration of the aqueous alkaline solution in step a) is adjusted to 10 to 30 wt. %, calculated in terms of the aminomethylphosphonic acid or salt thereof.

8. The method of claim 1 wherein for step b), use is made of 0.9 to 1.2 mol formaldehyde per mol of aminomethylphosphonic acid used in step a).

9. The method of claim 1, wherein step b) is carried out at the same pH and in the same temperature range as step a).

10. The method of claim 1, wherein for step c), hydrocyanic acid/or cyanide are used in an amount of 0.9 to 1.5 mol per mol of aminomethylphosphonic acid (salt).

11. The method of claim 1, wherein step c) is carried out at the same pH and temperature as step b).

12. The method of claim 1, wherein the hydrolysis is carried out in the presence of an inorganic or organic acid.

13. The method of claim 12, wherein concentrated hydrochloric acid is used as inorganic acid.

14. The method of claim 1, wherein for the hydrolysis, the inorganic or organic acid is used in a quantity of 4 to 8 mol per mol of aminomethylphosphonic acid or salt thereof.

15. The method of claim 1, wherein step d) is carried out at a temperature of 80 to 120° C.

16. The method of claim 1, wherein steps a), b), c) and d) are carried out in the form of a one-pot reaction.

17. The method of claim 1, wherein the N-phosphonomethyl glycine formed is isolated.

* * * * *